United States Patent

Melamud et al.

[19]

[11] Patent Number: 6,133,731
[45] Date of Patent: Oct. 17, 2000

[54] METHOD AND APPARATUS FOR THE ON-LINE MEASUREMENT OF THE STRENGTH OF METAL CABLES

[75] Inventors: Mordechai Melamud, Beer-Sheva; Gabriel Kohn, Omer, both of Israel

[73] Assignee: Case Technologies Ltd., Omer, Israel

[21] Appl. No.: 09/298,727

[22] Filed: Apr. 23, 1999

Related U.S. Application Data

[63] Continuation of application No. PCT/IL97/00323, Oct. 6, 1997.

[30] Foreign Application Priority Data

Nov. 7, 1996 [IL] Israel .......................................... 119579

[51] Int. Cl.$^7$ .......................... G01N 27/72; G01N 27/80; G01B 7/24; G01R 33/12
[52] U.S. Cl. .......................... 324/209; 324/232; 324/235; 324/242; 324/243
[58] Field of Search .................................. 324/209, 232, 324/235, 239–243; 73/862.69

[56] References Cited

U.S. PATENT DOCUMENTS

| | | | |
|---|---|---|---|
| 4,096,437 | 6/1978 | Kitzinger | 324/235 X |
| 4,495,465 | 1/1985 | Tomaiuolo et al. | 324/232 |
| 4,792,755 | 12/1988 | Huschelrath et al. | 324/242 X |
| 4,931,730 | 6/1990 | Olsen et al. | 324/209 |
| 5,008,621 | 4/1991 | Jiles | 324/243 X |
| 5,313,405 | 5/1994 | Jiles et al. | 324/209 X |
| 5,565,773 | 10/1996 | Inaguma et al. | 324/209 X |
| 5,619,135 | 4/1997 | Kohn et al. | 324/209 X |
| 5,804,964 | 9/1998 | Hamelin et al. | 324/235 X |

FOREIGN PATENT DOCUMENTS

| | | |
|---|---|---|
| 0 576 322 A1 | 10/1993 | European Pat. Off. . |
| 59104046 | 5/1984 | Japan . |
| 59271292 | 12/1984 | Japan . |

OTHER PUBLICATIONS

R. Rautioaho, J. Kivimaa and M. Moilanen, "Stress response of Barkhausen noise in high carbon steel cables and ropes", Journal of Magnetism and Magnetic Materials 129, 217–225 (1994) North–Holland.

J. Kivimaa, M. Moilanen, R. Rautioaho, H. Zhang, "Influence of Tensile Stress in Steel Cables on Magnetic Barkhausen Noise", 8108 IEEE Transactions on Magnetics 29 (1993) Nov., No. 6, New York, US.

*Primary Examiner*—Gerard Strecker
*Attorney, Agent, or Firm*—Akin, Gump, Strauss, Hauer & Feld, L.L.P.

[57] ABSTRACT

A method and an apparatus are provided for measuring the mechanical properties of ferromagnetic, elongated structures, such as cables, through the measurement of Barkhausen signals. The method comprises creating a magnetic field, that varies as a function of time or of position, and measuring the Barkhausen signals rate as a function of the magnetic field for each section of the structure to be tested. The mechanical properties are determined for each section from the Barkhausen signals relative to it. The apparatus comprises means for generating the variable magnetic field, a plurality of Barkhausen signal sensors distributed along the structure length, and means for comparing the signals relative to each section to be tested.

17 Claims, 9 Drawing Sheets

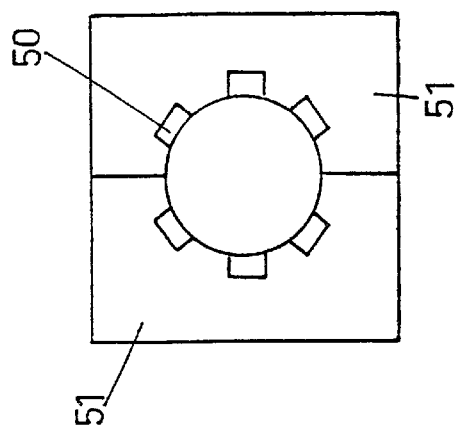
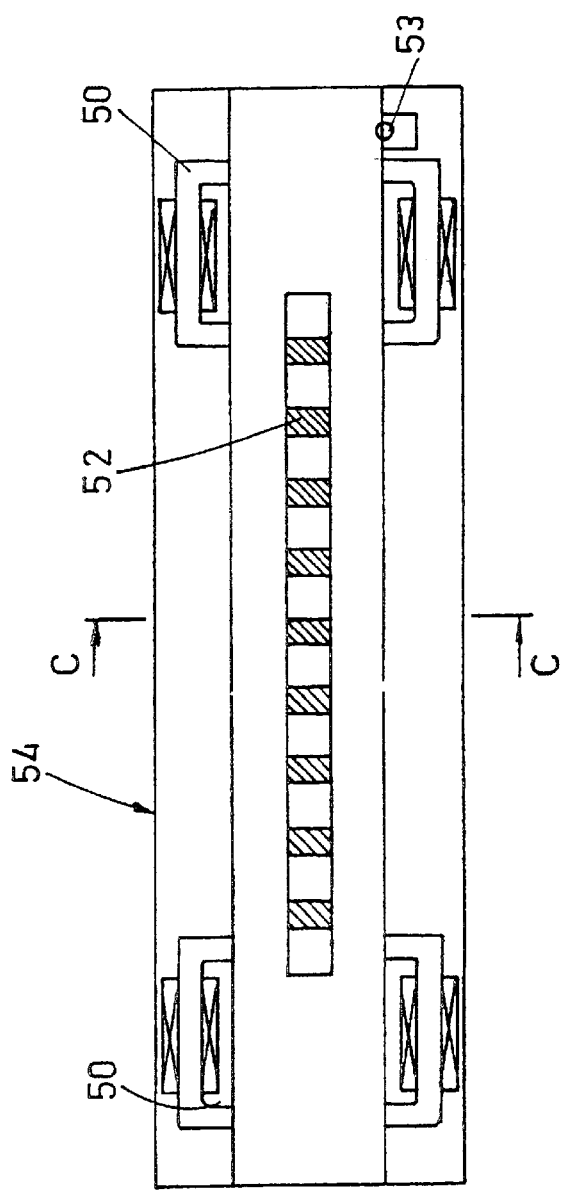
Fig. 5b
Fig. 5a

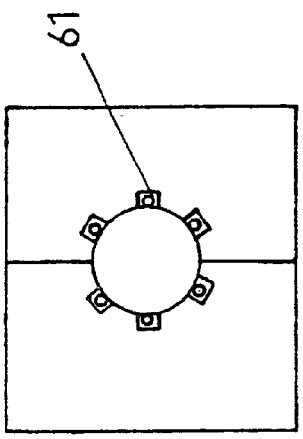
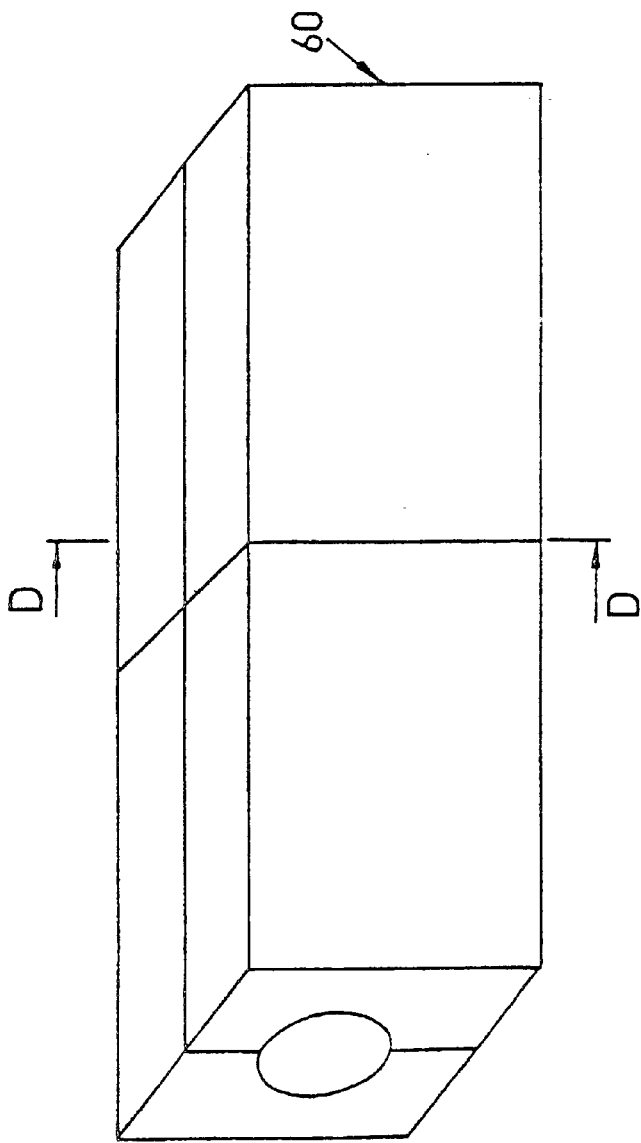
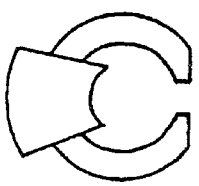
Fig. 6b
Fig. 6c
Fig. 6a

METHOD AND APPARATUS FOR THE ON-LINE MEASUREMENT OF THE STRENGTH OF METAL CABLES

CROSS REFERENCE TO RELATED APPLICATION

This application is a continuation of International Application PCT/IL97/00323, filed Oct. 6, 1997, the disclosure of which is incorporated herein by reference.

BACKGROUND OF THE INVENTION

The invention relates to a method and apparatus for measuring the mechanical properties, in particular yield strength, tensile strength and hardness, of metal cables or wires, in particular ferromagnetic cables or wires, during the production process or while in use, for lifting or conveying loads or supporting and transporting loads, for example in cable cars. The method to which the invention relates is also applicable for detecting aging in static applications, such as in pretensioned reinforced concrete or controlling the properties of tubular steel products such as pipes, and in all cases in which it is possible to produce relative motion between a control apparatus and the ferromagnetic structure that is being controlled.

It is of great importance, both for economical, technological and safety reasons, to be able to measure the mechanical properties, particularly the yield strength and tensile strength, of cables on line. While this is very useful in the production of the cables, to control their quality continuously and synchronously with the production rhythm, it is even more important when the cable is in use for lifting loads, such as in loading or unloading or salvaging operations, or for supporting and transporting persons, such as in cable cars, since the breakage of a cable may involve not only extreme economic loss, but also the loss of life.

The art provides no reliable method for measuring the yield strength or the tensile strength of steel cables. Destructive methods permit only testing of small portions of the cable and provide no protection against failures due to non-uniform properties of the cable. Further, they are not applicable to cables in use. Cables coming off a production line are tested using a small number of specimens and, once again, there is no way of accounting for non-uniformity between different specimens. Cables in use are tested only visually and it is obvious that visual testing is highly inadequate. The only alternative testing methods for steel cables, presently applied, are based on magnetic flux leakage and can only locate broken wires and loss of metallic area (LMA) of the cable. Therefore, the art does no permit control of the properties of an entire cable while in use.

A phenomenon known as the Barkhausen effect has been described extensively in the literature, e.g., in the paper by Swartzendruber et al. (*J. Appl. Phys.* 67, No. 9, 5469–5471 (1990). This effect consists of the large number of irreversible jumps in magnetization that occur while a ferromagnetic material is subjected to a varying magnetic field. The jumps are due to the unpinning of domain wall structures from defects and impurities in the material. As the applied field increases, a wall breaks away from one pinning site and moves rapidly until stopped by another pinning site. The resultant jumps in magnetization, which have the characteristic of a noise signal, can be detected by suitable sensors as described, for example, by Swartzendruber and Hicho in a separate paper (*Res. Nondestr. Eval* (1993) 5, 41–50).

Since the pinning sites of the domain walls, i.e., dislocations and impurities, also affect the mechanical properties of the steel, it is possible to correlate the Barkhausen signal with the mechanical properties of metals. Thus, the art describes the application of the Barkhausen effect to determine properties of metals based on relationships existing between the Barkhausen signals and said properties. For example, in U.S. Pat. Nos. 4,599,563, the Barkhausen signals are used to determine properties of steel. U.S. Pat. Nos. 4,689,558, 4,977,373 and 4,881,030 disclose the determination of residual stress or fatigue limit in steel and like materials, based on the Barkhausen signals. U.S. Pat. No. 5,313,405 discloses a system for non-destructive evaluation of the surface characteristics of a magnetic material, comprising probe means magnetically-coupled to a sample of the material for applying an alternating magnetic field at a plurality of frequencies selected to excite Barkhausen domains at different levels, near but below the surface of the sample, means for detecting a complex Barkhausen response of the sample for more than one frequency, and processor means for analyzing the characteristics of said responses to isolate at least frequency and amplitude information from each response for determination of the surface characteristics of the sample.

Other pertinent publications dealing with the measurements of mechanical properties of ferromagnetic materials are Karjalainen et al., "Detection of Fabrication Stresses by the Barkhausen Method, Effects of Fabrication Related Stresses", September 1985, pp. 149–161 and Kaplan et al., "Nondestructive Evaluation of Ferromagnetic Materials by Magnetometer-Like Experimental Arrangement", *Journal of Nondestructive Evaluation*, Vol. 6, No. 2, 1987, pp. 73–79.

In a recent paper by Thompson and Tanner (JMMM (1994)132, 71–88), measurements were made on low carbon steels of the Vickers hardness as a function of plastic deformation, and also of the coercivity as a function of plastic deformation, both to rather high values of deformation.

Coercivity can be measured by recording the magnetization of the sample as a function of variable applied magnetic field (hysteresis loop); in this case, the coercivity is determined as the value of applied field at which the magnetization of the measured sample is zero. The coercivity of ferromagnetic steel can also be estimated by the measurement of the Barkhausen signal rate (BSR) as a function of variable applied magnetic field. It can be shown that a maximam in the BSR occurs near the coercive field as the applied field is changed.

J. Kivimaa et al., "Influence of Tensile Stress in Steel Cables on Magnetic Barkhausen Noise," *IEEE Transactions on Magnetics*, Vol. 29, no. 6, 1993, pp. 2992–2994, describes the application of the magnetic Barkhausen noise (BN) method for stress measurement in ferromagnetic steel cables. R. Ratitioaho et al., "Stress response of Barkhausen noise in high carbon steel cables and ropes", *Journal of Magnetism and Magnetic Materials*, vol. 1239, no. 2–3, pp. 217–225, describes a similar application in particular for steel concrete reinforcement cables. Both of these articles find that Barkhausen noise decreases with increasing tension. Neither of them, however, relates to the measurement of inherent mechanical properties of steel cables, particularly yield and/or tensile strength.

None of the prior art publications, however, disclose systems that are applicable to the on-line measurement of the mechanical properties, particularly yield strength and tensile strength, of elongated or filamentary structures, such as cables, of ferromagnetic materials, particularly steel. In particular, none of them discusses the effect of stresses and strains in the plastic range on the Barkhausen signal or any correlation between this signal and the mechanical propertes of steel cables. On-line control of steel cables, not only in the production line, but in actual use as well, is of paramount importance and presents difficulties which the prior art has not even considered. Spot checks and/or measurements providing average values of mechanical parameters provide no reliable information as to possible local defects or weak points, that may cause the failure of the cable when in use.

It should be noted that metal cables may fail due to one or more of the following causes:

abrasion and crushing, due to contact of the cable with an abrading medium or to its being subjected to severe mechanical pressure; corrosion, due to corrosive environment; broken or cut strands, due to fatigue or mechanical damage, or to a high overload beyond the load-bearing capacity of the cable; shock loading or overloading; and overheating or fatigue.

Some of the above failure causes, e.g., overloading, overheating or fatigue, will affect the strength of the cable and still not be detected by current available non-destructive test methods.

It is therefore a purpose of this invention to provide a method and apparatus for determining the mechanical properties of cables of ferromagnetic material, that is applicable on-line, both in production and in use.

It is another purpose of this invention to provide such a method and apparatus which is applicable to a single wire as well as to a multiple strand cable.

It is a further purpose of this invention to provide such a method and apparatus which is applicable to multiple strand cables comprising strands of different ferromagnetic materials.

It is a still further purpose of this invention to provide such a method and apparatus that is effective in localizing weak sections of the cable where failure is likely to occur.

It is a still further purpose of this invention to provide such method and apparatus that is relatively inexpensive and simple to make.

It is a still further purpose of this invention to provide such a method which detects changes in the strength of the cable and will permit predicting the occurrence of events, which may lead to cable failure, even before they happen.

It is a still further purpose of this invention to provide such a method and apparatus that are effective in localizing sections of a cable where cable strength has changed or/and does not comply with the standard.

Other purposes and advantages of the invention will become apparent from the following detailed description.

SUMMARY OF THE INVENTION

The method of the invention for measuring the mechanical properties, particularly yield strength and tensile strength, of ferromagnetic elongated structures, particularly cables, comprises the following steps:

creating at least a magnetic field that varies either as a function of time or as a function of position or both, along at least a given length of the structure;

for each section of the structure to be tested, sensing a plurality of Barkhausen signals (hereinafter also indicated by "BS") due to the time or position related variation of said magnetic field;

measuring the BS rate (hereinafter also indicated by "BSR") as a function of the value of the magnetic field applied to each said section; and determining the desired mechanical properties, particularly yield strength and tensile strength, of each such section from said sensed Barkhausen signals relative to it.

The word "cable", as used herein, should be construed as including any other elongated or filamentary structure, such as a wire or the like. whether endless, as on a production line, or having a definite length, as in use.

The mechanical properties of the structure may be determined from the Barkhausen signals by calculation, if a definite functional relationship from said signals and said properties exists and is known. But in many cases this is difficult or even impossible. This may be true, for example, with reference to defects or damages that may affect a structure, and yet are not related to the numerical value of a specific mechanical property. Therefore, in a preferred embodiment of the invention, the properties of the tested structure are determined by creating a series of reference samples, having the defects or having undergone the damages that are relevant and likely to have occurred in the particular tested structure, depending on the way it has been made, on its use and age, and on its history in general said reference samples are checked according to the procedure and by the means of this invention, the resulting diagram representing the Barkhausen, signals are stored, and any tested structure is subjected to same procedure, the diagram referring to it is compared to those of the reference samples and it is determined which are the reference samples that are closest to the tested structure. If the diagram of this latter is practically the same or very close to that of a reference sample, this provides the required information, as the tested structure can be assumed to have substantially the same relevant properties as those of the reference samples. Otherwise, if the diagram of the tested structure is intermediate between those of two reference samples, the tested structure can be assumed to have properties intermediate between those of said two samples. One may say that, for every relevant defect or damage, a reference scale is provided, and the position of the tested structure in said scale is determined by interpolation. The same method can be used, of course, to determine mechanical parameters of structures that are free of defects or damages or mechanical parameters that are independent of defects or damages.

The magnetic field as has been said, may vary either as function of time, as a function of position, or as a function of both. From this viewpoint, there are three main forms of the invention. In the first form, the Barkhausen sensor will measure the BSRs as a function of a magnetic field which varies only with time. A device for measuring the field strength, e.g., a Hall probe, will be provided and incorporated in the apparatus according to the invention. Successive measurements of BSR will be taken at different values of the inducing magnetic field, viz. at different times, since the field is a function of time only. From the apparatus viewpoint, in this form of the invention, the driving field is produced by at least an electromagnet fed with an alternating current, at least a sensor is provided in a fixed position with respect to the electromagnet, the cable is stationary with respect to the apparatus unit constituted by the electromagnet and the sensor, and the time, with respect to which the BSR is measured, is recorded. The dimensions of the electromagnet and of the sensor are also measured, as they determine the length of the cable element which is subjected to the BSR measurement during the time required to acquire the minimum needed amount of BS. In the following forms of the invention, in which the cable is in motion with respect to the apparatus unit, the relative speed of the cable with respect to said unit is measured, in addition to the dimensions of the electromagnet and of the sensor.

In a second form of the invention, the magnetic field is generated by at least an electromagnet fed with an alternating current, and the magnetic field is therefore variable with time, at least a BS sensor is provided in a fixed position with respect to the electromagnet viz. the apparatus unit constituted by the electromagnet and the sensor is the same as in the first form of the invention but the cable is in motion with respect to said apparatus. The measured BSR, therefore, depends both on the instant value of the magnetic field and on the speed of the cable, with respect to the said apparatus unit.

In a third form of the invention, the magnetic field is generated by permanent magnets and a string or row of sensors is spaced along the axis of the magnet system, which coincides with the axis of the cable. In such a way, the sensors are positioned at points at which the induced magnetic field has different values. The applied field values will be precalibrated at the position of each sensor, so that it will be possible, though not necessary, to use a field strength measuring device. The cable is in motion with respect to the apparatus constituted by the said magnets and the said string of sensors. The string of sensors will provide, in their various measurements at different times, signals relative to different cable elements, since the cable is in motion along the axis, of the apparatus with respect to the sensors. Correct processing will permit to relate the signals to a certain cable element as it travels along the system at the different field values. Processing the sensors' output at time intervals, which are coordinated with their spacing and with the cable speed, will supply the data as a function of field for each cable element. The same result can be achieved by periodically reading all sensors and rearranging the data by means of a computing unit.

In all forms of the invention, the results of the measurements will consist of a set of values of BS at different values of the applied magnetic field. The BSR, that is, the number of BS per seconds occurring at the sensor at a few, at least four, applied field values will be recorded. These will be fitted to a Gaussian type or similar function. The location of the first moment (viz., the average) of this function with respect to the applied field is calculated by a computer. The strength (UTS) or hardness of the tested cable section, may be subsequently calculated by comparing the results to those obtained from a similar cable of known mechanical properties; or the other procedures explained hereinbefore may be resorted to.

The apparatus according to the invention comprises:
  means for generating a magnetic field that varies along at least a given length of the elongated structure;
  a plurality of Barkhausen signal sensors distributed along said structure length;
  means for comparing the signals relative to each section of the structure to be tested; and, optionally,
  computer means for elaborating the said signals to determine the relevant mechanical properties, e.g. to calculate yield strength and tensile strength, of each such section from said sensed Barkhausen signals relative to it.

The apparatus preferably includes means for measuring its speed relative to the cable, generally for measuring the speed of the cable, if the apparatus is stationary, or that of the apparatus itself if the cable is stationary.

When the means for generating magnetic fields are permanent magnets, they may preferably be of annular shape and surrounding the cable. Electromagnets may have a similar or any other convenient structure and shape.

In an embodiment of the invention, each sensor comprises a number of individual sensor elements mounted on an annular support which surrounds the traveling cable and is essentially coaxial with it and several sensors, of such or of a different structure, are preferably positioned along the cable as a "string", at different field intensities.

If the invention is applied to on-line testing in production line, the electromagnets or permanent magnets and the sensors are stationary and placed at any convenient position along the line, towards the end of it. If the invention is applied to a machine or equipment in which only a certain portion of a cable is unrolled from a support and re-rolled on it, such as in a crane, this is the portion that will be tested, preferably by means of a portable apparatus unit, according to the invention, placed in each case in the most suitable position If the invention is applied to a stationary cable, an apparatus unit that moves along the cable will be employed.

In cable car and some other applications there are two types of cables: a stationary and a moving one. For each type, the appropriate testing apparatus fixed or movable and of the appropriate shape will be used.

While the method and apparatus of the invention have been defined with reference to a cable or wire or the like, they can be applied for testing other elongated ferromagnetic structures, such as pipes.

BRIEF DESCRIPTION OF THE SEVERAL VIEW OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIGS. 5a and 5b are schematic representations, in axial and transverse cross-section along plane C—C, respectively, of an apparatus according to a fifth embodiment of the invention;

FIGS. 6a and 6b are schematic representations, in perspective view and transverse cross-section along plane D—D, respectively, of an apparatus according to a sixth embodiment of the invention, and FIG. 6c is a detail of FIG. 6b at an enlarged scale;

DETAILED DESCRIPTION OF THE INVENTION

Figure 1:
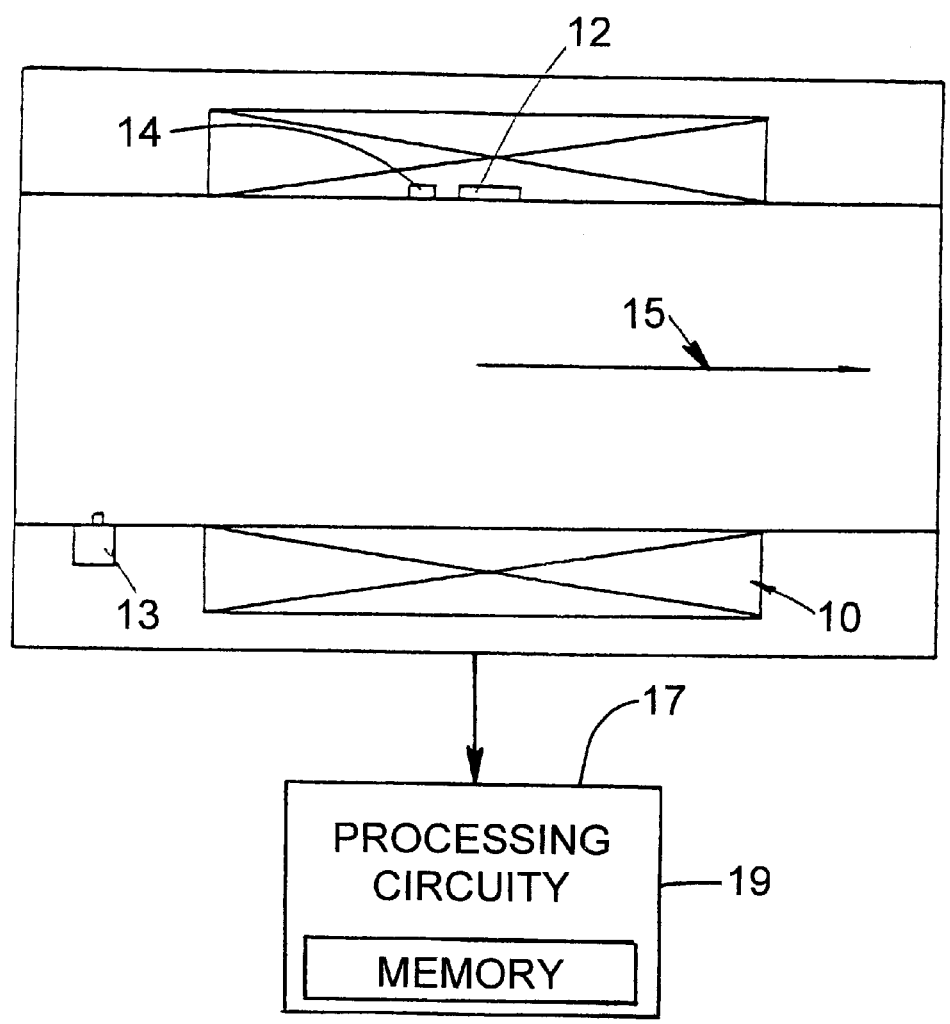
FIG. 1 is a schematic representation in axial cross-section of an apparatus according to a first embodiment of the invention.

With reference now to FIG. 1, the apparatus according to a first embodiment of the invention comprises a single electromagnet 10, fed with alternating current, encircling the tested cable (not shown), 12 indicates a Barkhausen sensor. The cable is in motion with respect to the apparatus, as indicated by arrow 15. The apparatus includes a Relative Cable-Sensor Speed (RCSS) measuring unit 13 and a field strength measuring unit (e.g., Hall probe 14) to measure the magnetic field applied to the cable. In all embodiments, measurements are taken consisting of a set of values of BS at different values of the applied magnetic field. The BSR, that is, the number of BS per seconds, occurring at the sensor at a few, at least four, applied field values, are recorded. The BS rates are fitted to a Gaussian type or similar function. The location of the first moment (viz., the average) of the selected function with respect to the applied field is calculated by a computer having a processing circuit 17 and a memory 19. The strength (UTS) or hardness of the tested cable section, may subsequently be calculated by comparing the results obtained from the tested ferro-magnetic material to results obtained from a similar cable of known mechanical properties stored in a lookup table, for example within the memory 19. In all embodiments, although not shown, a computer having a processing circuit and memory receives measurements of a set of Barkhausen signals at different values of the applied magnetic field.

Figure 2B:
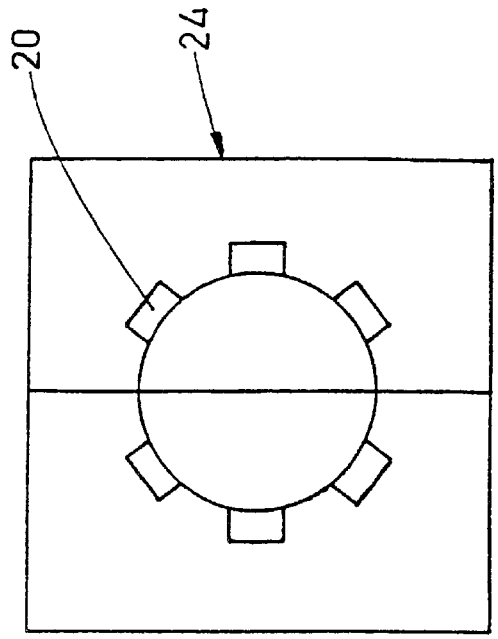
FIGS. 2a and 2b are schematic representations, in axial and transverse cross-section along plane A—A, respectively, of an apparatus according to a second embodiment of the invention.
Figure 2A:
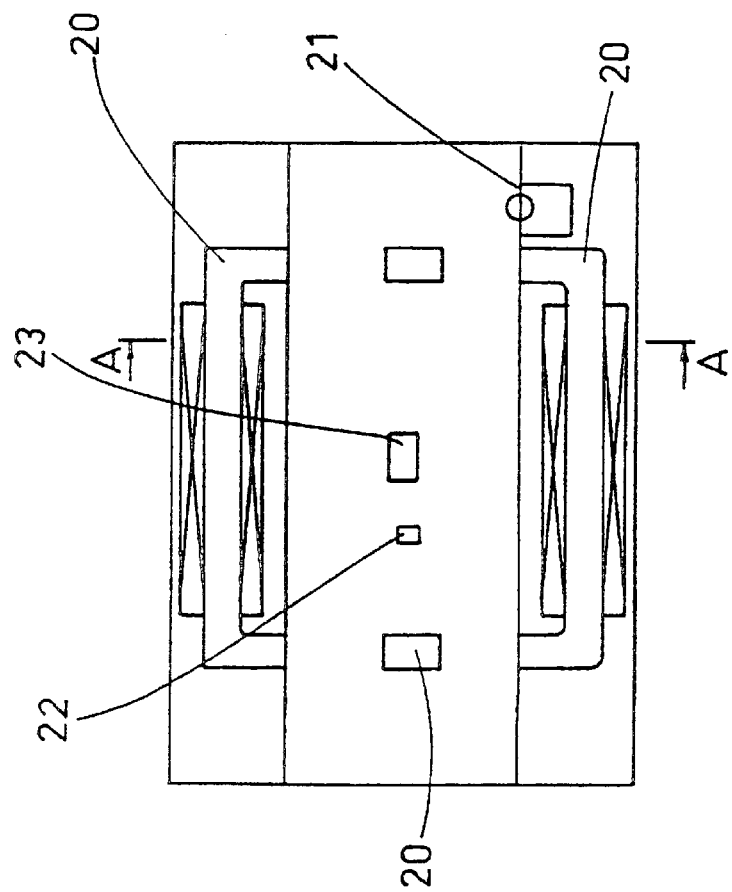

FIGS. 2a and 2b illustrate another embodiment of apparatus, comprising a circumferential array of U-shaped AC electromagnets 20. The apparatus includes an ROSS measuring unit 21 and a field strength measuring unit (e.g., Hall probe 22) to measure the magnetic field applied to the cable. This apparatus is designed in such a way that it can be opened (split) in order to encircle an installed cable, as schematically shown in cross section in FIG. 2b. The apparatus includes at least two, but preferably six, as shown in the drawing, U-shaped electromagnets 20 of the same polarity, applying a homogeneous magnetic field along the cable axis, 23 designates a Barkausen sensor. The apparatus has a casing 24 in two separable halves, for access to its components.

Figure 3B:
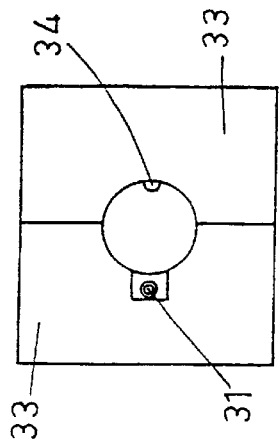
FIGS. 3a, 3b and 3c are schematic representations, in axial and transverse cross-section along plane B—B and in perspective view, respectively, of an apparatus according to a third embodiment of the invention.
Figure 3A:
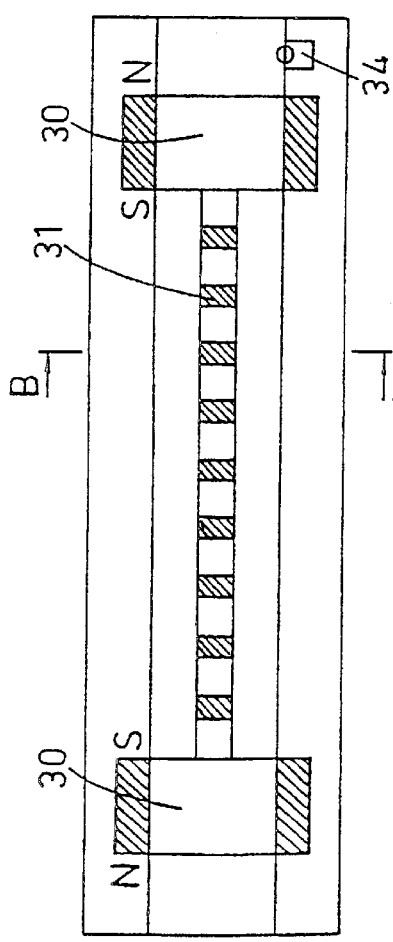
Figure 3C:
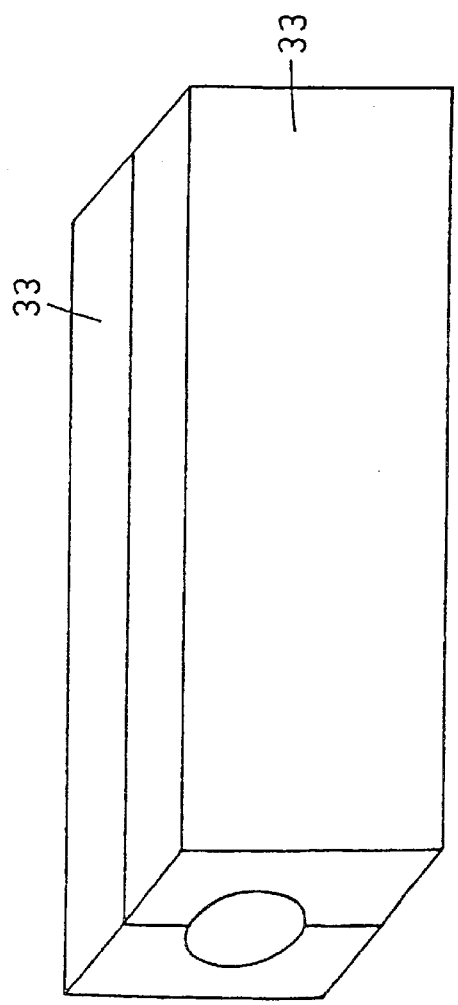

A third embodiment of the apparatus according to the invention, illustrated in FIGS. 3a, 3b and 3c, includes a number of permanent magnets 30. They are at least two, they fully encircle the cable (not shown) and are magnetized parallel to their axis. These are arranged along the path of the tested cable (not show) with opposing magnetic poles facing each other, as designated by S and N in the drawing. A few Barkhausen sensors 31 (at least four) are spaced equally between the magnets along the axis of the apparatus viz. the tested cable path, at positions of known (preset) values of the applied magnetic field. The magnets are split so that it is possible to open the apparatus, consisting of two halves 33, in order to encircle the tested cable. A Relative CableSensor Speed (RCSS) measuring unit 34 is placed inside the apparatus housing to measure the speed of the cable relative to the sensor. Both the magnets and sensors are mounted on adjustable mounts so as to fit various cable diameters.

Figure 4:
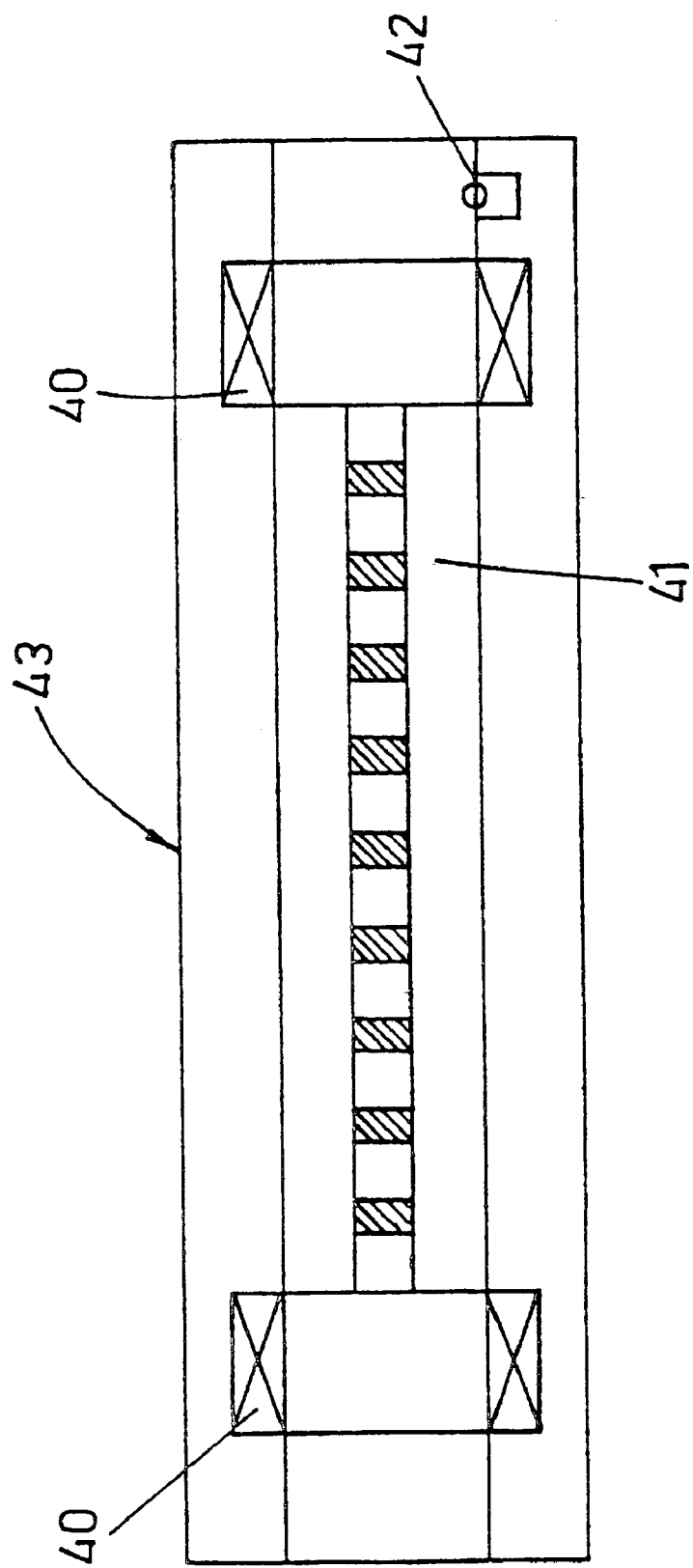
FIG. 4 is a schematic representation in axial cross-section of an apparatus according to a fourth embodiment of the invention.

A further embodiment, slightly different from the previous one, of the apparatus of the invention is schematically shown in FIG. 4. It contains at least two DC electromagnets 40, Barkhausen sensors 41 and RCSS 42, mounted on a casing 43. This apparatus cannot be opened so as to be mounted around a cable, and is therefore intended to be used on the production line of wire ropes (not shown), or at least any other installation where the tested wire rope can be inserted through the apparatus.

A fifth embodiment of the apparatus of the invention is schematically shown in FIGS. 5a and 5b. It includes at least two circumferential arrays of U-shaped DC electromagnets 50, placed around the cable path and mounted on a casing 54, instead of the electromagnets of FIG. 4. This apparatus can be opened, as it comprises a housing in two halves 51, and placed around an installed cable at any suitable test location. It also comprises Barkhausen sensors 52 and a RCSS 53.

As to the components of the above embodiments, Barkhausen Signal sensor units are described in the literature (e.g., L. J. Swartzendruber and G. E. Hicho, *Res. Nondestr. Eval.* (1993), 5, 41–50). Each comprises a ferrite core in the shape of a toroid with a coil wound around it. The toroid is ground flat on one side to provide a gap. This is an example of Barkhausen Signal sensor and there are differently built such sensors.

A circumferential assemblage sensor can be built of a few Barkhausen signal sensor units arranged on a ring. One such arrangement is schematically shown in FIGS. 6a, 6b and 6c, wherein 60 is the apparatus housing and 61 are the sensor units, one of which is shown at an enlarged scale in FIG. 6c.

An encircling sensor can consist of a coil wound around a cylindrical path in which the tested cable moves, and can be made according to the teaching of the above reference.

Figure 7:
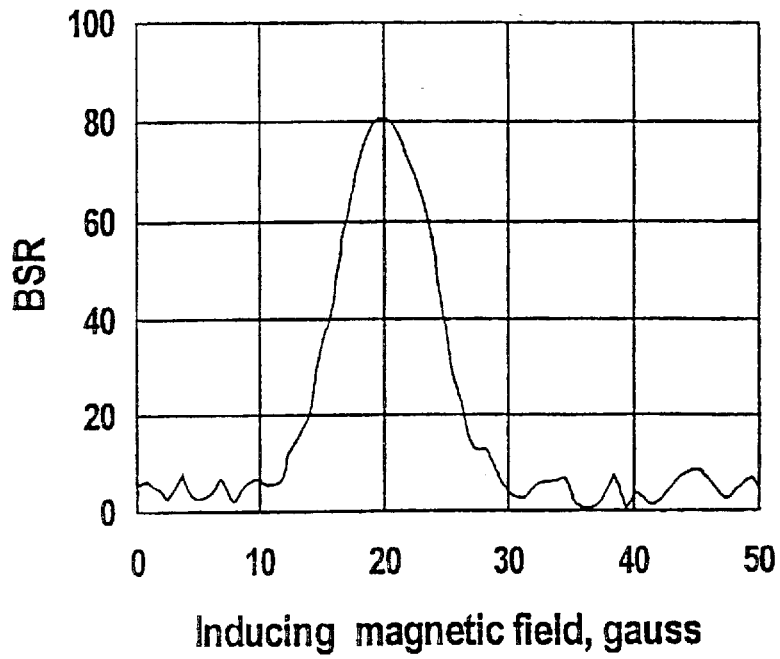
FIGS. 7 to 10 are diagrams representing the BSR as a function of the inducing magnetic field intensity, for different tested structures.

FIG. 7 shows a typical BSR. The location (e.g., center of peak) of the BSR peak with respect to the applied magnetic field is directly related to the strength (UTS) of the cable or wire.

Figure 8:
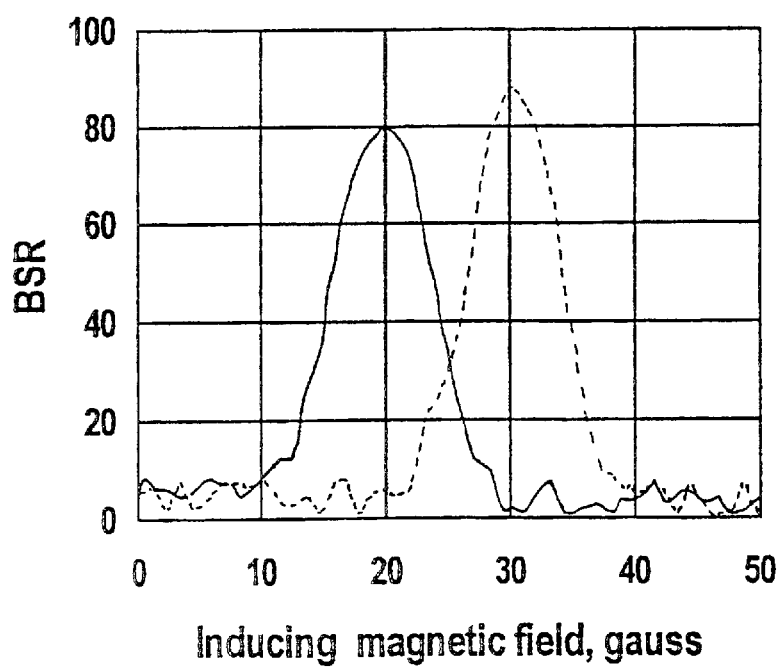

A wire or cable having low UTS will have its peak located at a smaller inducing magnetic field when compared with a similar wire with a higher UTS. This is illustrated in FIG. 8. The curve in full line refers to a metal sample having lower UTS than that of the sample to which the curve in broken lines refers.

Figure 9:
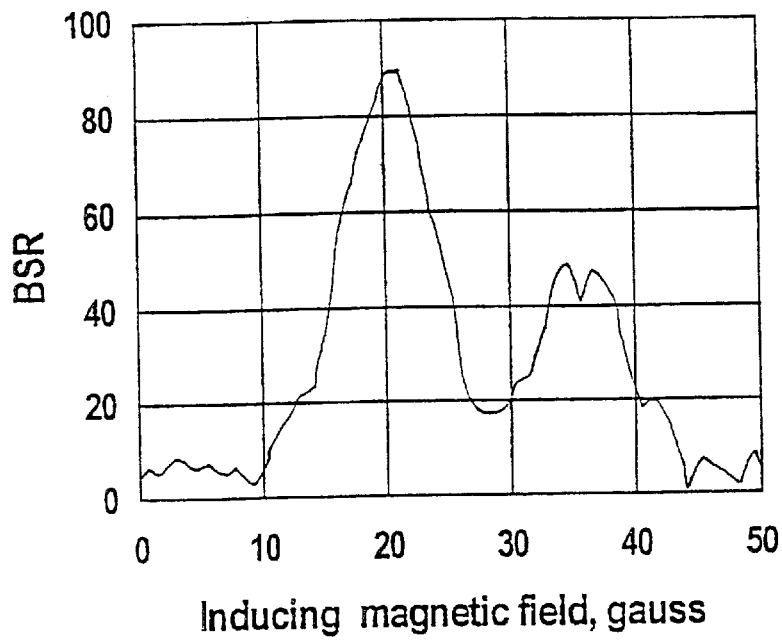
Figure 10:
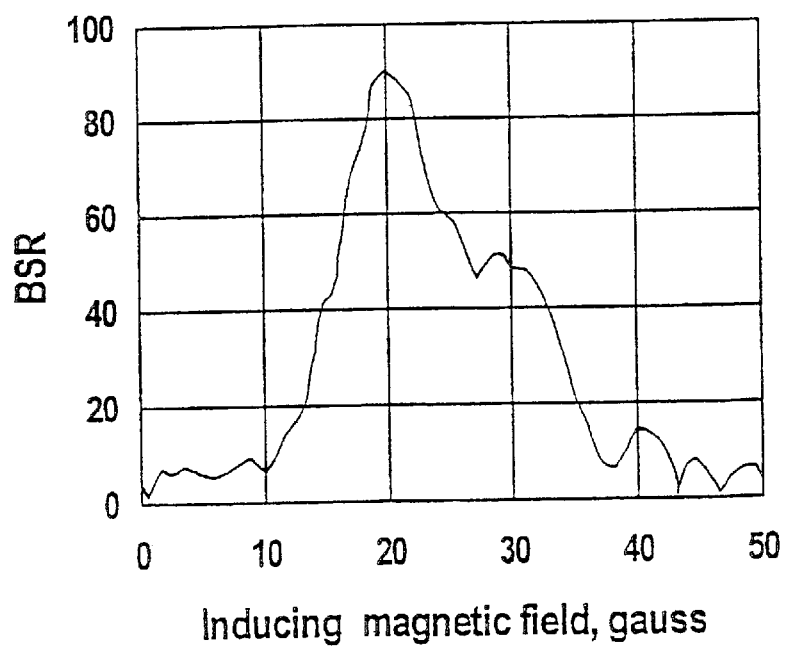

In the cases in which a cable consists of at least two types of steel wires (or of wires having two different values of UTS), the diagram of the BSR vs. the applied field will have a double hump, as seen in FIG. 9 or 10.

Figure 11:
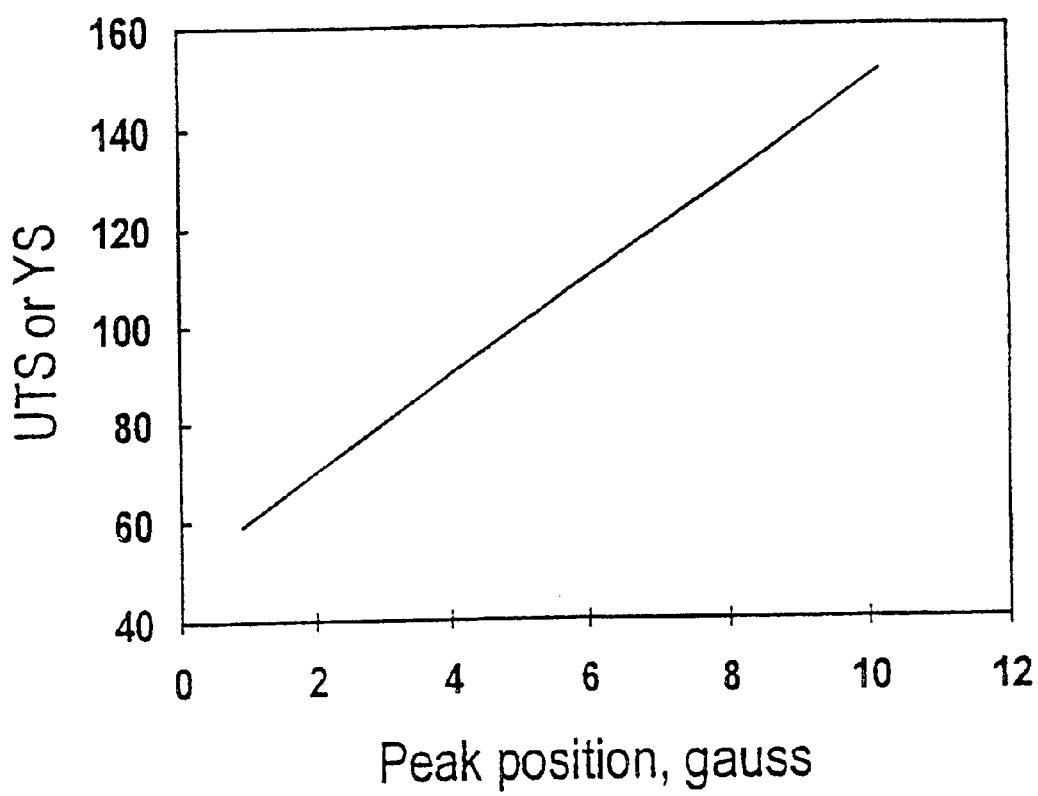
FIG. 11 is a diagram showing a typical relationship of UTS or YS to the BSR peak position.

The location of the center of the BSR peak with respect to the applied field is linearly related to the strength of the cable, as shown in the diagram of FIG. 11.

While specific examples of the invention have been described by way of illustration, it will be apparent that the invention can be carried out by persons skilled in the art with many modifications, variations and adaptations, without departing from its spirit or exceeding the scope of the claims.

We claim:

1. Method for measuring the yield strength and/or tensile strength of ferromagnetic, elongated structures, including cables, the method comprising the steps of:

creating at least a magnetic field that varies either as a function of time or as a function of position or both, along at least a given length of the structure;

sensing a plurality of Barkhausen signals due to the time or position related variation of said magnetic field for each of a plurality of sections of the structure to be tested, measuring a set of values of the Barkhausen signal rate as a function of the value of the applied magnetic field for each said section; and determining the yield strength and/or tensile strength of each such section from said sensed Barkhausen signal rate measured for said section by calculation or by comparing the set of values to reference values obtained from a series of reference samples with known properties.

2. The method according to claim 1, wherein the magnetic field varies as a function of time only.

3. The method according to claim 1, wherein the magnetic field varies as a function of position only.

4. The method according to claim 1, wherein the magnetic field varies as a function both of time and of position.

5. The method according to claim 1, wherein the structure is a cable or wire.

6. The method according to claim 1, wherein the structure is stationary with respect to the magnetic field.

7. The method according to claim 1, wherein the structure is in motion with respect to the magnetic field.

8. An apparatus for measuring yield strength and/or tensile strength of elongated, ferromagnetic structures, comprising:

means for generating a magnetic field that varies along at least a given length of the elongated structure;

at least one Barkhausen signal sensor along a section of said structure length for taking measurements of a set of values of Barkhausen signal rates at different values of the applied magnetic field; and means for determining the yield strength and/or tensile strength of the structure from the Barkhausen signal rate sensed at the section by calculation or by comparing the set of values to reference values obtained from a series of reference samples with known properties.

9. The apparatus according to claim 8, wherein the electromagnet field is generated by an alternating current.

10. The apparatus according to claim 9, wherein at least one sensor is in a fixed position with respect to the electromagnet.

11. The apparatus according to claim 10, further comprising a device for measuring electromagnetic field strength.

12. The apparatus according to claim 8, further comprising a plurality of permanent magnets, placed along an axis, a string of sensors spaced along said axis, and means for causing the apparatus to travel along the axis.

13. The apparatus according to claim 8, further comprising means for registering the output of the sensors.

14. The apparatus according to claim 8, wherein the sensors are symmetrically distributed around the structure.

15. The apparatus according to claim 8, wherein the means for determining the yield strength and/or tensile strength of the structure is either computer means calculating said yield strength and/or tensile strength from said signals or means for comparing the Barkhausen signals obtained from said structure to the corresponding signals obtained from reference samples.

16. The apparatus according to claim 8, wherein each sensor comprises a number of individual sensor elements mounted on an annular support which surrounds the structure and is essentially coaxial with it and several such sensors are positioned along the structure, at different field intensities.

17. The apparatus according to claim 8, wherein the elongated structure is a cable.

* * * * *